United States Patent
Le Bras et al.

(10) Patent No.: US 7,801,350 B2
(45) Date of Patent: Sep. 21, 2010

(54) METHOD FOR ABSORPTIOMETRY RADIOGRAPHIC IMAGING USING A THREE-DIMENSIONAL GENERIC MODEL

(75) Inventors: Anthony Le Bras, Quimperle (FR); Sami Kolta, Sucy en Brie (FR); David Mitton, Le Kremlin Bicetre (FR); Wafa Skalli, Paris (FR); Jacques A. De Guise, Montreal (CA); Christian Roux, Paris (FR); Sébastien Teysseyre, Paris (FR); Jacques Fechtenbaum, Paris (FR)

(73) Assignee: Biospace Instruments, Paris (FR)

( * ) Notice: Subject to any disclaimer, the term of this patent is extended or adjusted under 35 U.S.C. 154(b) by 1219 days.

(21) Appl. No.: 10/540,107

(22) PCT Filed: Nov. 27, 2003

(86) PCT No.: PCT/EP03/14845

§ 371 (c)(1),
(2), (4) Date: Jun. 20, 2005

(87) PCT Pub. No.: WO2004/056270

PCT Pub. Date: Jul. 8, 2004

(65) Prior Publication Data

US 2006/0204069 A1    Sep. 14, 2006

(30) Foreign Application Priority Data

Dec. 20, 2002   (FR) .................................. 02 16320

(51) Int. Cl.
*G06K 9/00*   (2006.01)
(52) U.S. Cl. ...................................... 382/132

(58) Field of Classification Search ......... 382/128–134; 378/53–56, 145–155, 193–198; 128/653.1, 128/922; 250/455–465; 356/39–49; 600/407, 600/408, 409, 410, 411, 412, 413, 414, 424, 600/425, 426

See application file for complete search history.

(56) References Cited

U.S. PATENT DOCUMENTS

| 4,029,963 | A | 6/1977 | Alvarez et al. |
| 4,811,373 | A | 3/1989 | Stein |

(Continued)

FOREIGN PATENT DOCUMENTS

FR    2798260    3/2001

(Continued)

OTHER PUBLICATIONS

French Preliminary Search Report dated Sep. 4, 2003 received in French patent application No. FR 0216320.

(Continued)

*Primary Examiner*—Samir A. Ahmed
*Assistant Examiner*—A. Fitzpatrick
(74) *Attorney, Agent, or Firm*—Marshall, Gerstein & Borun LLP (57) ABSTRACT

Method for radiographic imaging, in particular for measuring the bone mineral density of an osseous body, this method involving an operation which consists in determining the value of a composite index using, on the one hand, digitized radiological data, and, on the other hand, a three-dimensional generic model of said osseous body.

25 Claims, 5 Drawing Sheets

U.S. PATENT DOCUMENTS

| | | | |
|---|---|---|---|
| 5,483,960 | A | 1/1996 | Steiger et al. |
| 5,673,298 | A | 9/1997 | Mazess |
| 5,687,210 | A | 11/1997 | Maitrejean et al. |
| 5,768,334 | A | 6/1998 | Maitrejean et al. |
| 5,771,272 | A | 6/1998 | Berger et al. |
| 5,778,045 | A | 7/1998 | von Stetten et al. |
| 5,838,765 | A | 11/1998 | Gershman et al. |
| 5,850,836 | A | 12/1998 | Steiger et al. |
| 6,324,252 | B2 | 11/2001 | Siffert et al. |
| 6,438,201 | B1 * | 8/2002 | Mazess et al. ............... 378/56 |
| 6,529,582 | B2 | 3/2003 | Feldmesser et al. |
| 2002/0075997 | A1 * | 6/2002 | Unger et al. ............... 378/98.9 |
| 2003/0112921 | A1 * | 6/2003 | Lang et al. ................... 378/54 |

FOREIGN PATENT DOCUMENTS

| | | |
|---|---|---|
| WO | WO 02/38045 | 5/2002 |
| WO | WO 03/065772 | 8/2003 |

OTHER PUBLICATIONS

Abstract of "Precision Bone and muscle loss measuerments by advanced, multiple projection DEXA (AMPDXA) techniques for spaceflight applications", Charles et al., from teh Pub. Med. Data base.

"Vertebral Fracture Assessment Using a Semiquantitative Technique", Genant et al, Journal of Bone Mineral Research, 1993.

"Densitometrie du tissue osseux", Roux, Encl. Med, Chir. Elsevier, Paris, Radiodiagnostic, Squelette normal, 30-230-1990.

"Simple Measurement of Femoral Geometry Predicts Hip Fracture: The Study of Osteoporotic Fractures", Faulkner et al., Journal of Bone and Mineral Research, 1993.

"Femoral Neck Geometry and Radiographic Signs of Osteoporosis As Predictors of Hip Fracture", Karlsson et al., Bone, vol. 18, No. 4, Apr. 1996.

"Different Morphometric and Densitometric Parameters Predict Cervical and Trochanteric Hip Fracture: The EPIDOS Study", Duboeuf et al., Journal of Bone and Mineral Research, 1997.

"Racial Differences in Hip Axis Lengths Might Explain Racial Differences in Rates of Hip Fracture", Cummings et al., Osteoporosis International, 1994.

"3D Reconstruction Method From Biplanar Radioraphy Using Non-stereocorresponding Points and Elastic Deformable Meshes", Miton et al., Medical and Biological Engineering and Computing, 2000, vol. 38.

"The Effect of 3D-XA Derived Geometric Parameters and Proximal Femur Failure Load Prediction", Le Bras et al., 25th Annual Meeting of American Society for Bone and Mineral Research (ASBMR), Sep. 19-23, 2003, Minneapolis, MN.

"3 Dimensional X-ray Absorptiometry (3D-XA): Validation of 3D Reconstruction of Human Proximal Femurs Using a DXA Device", Kolta et al., ASBMR, Sep. 19-23, 2003, Minneapolis, MN.

"3 Dimensional X-ray Absorptiometry (3D-XA): Validation of 3D Reconstruction of Human Vertebrae Using a DXA Device", Kolta et al., ASBMR, Sep. 19-23, 2003, Minneapolis, MN.

* cited by examiner

METHOD FOR ABSORPTIOMETRY RADIOGRAPHIC IMAGING USING A THREE-DIMENSIONAL GENERIC MODEL

FIELD OF THE INVENTION

The present invention relates to methods and devices for radiographic imaging, in particular for measuring bone mineral density.

DESCRIPTION OF THE RELATED ART

More particularly, the invention concerns a method for radiographic imaging comprising a step (d) which consists in introducing, into calculation means, first digitized radiological data from signals delivered by means of detection of X-rays and corresponding to pixels of a first image of an anatomical part comprising an osseous body and scanned, in a first incidence, with a beam of X-rays having an energy spectrum distributed about at least two energies, these first data comprising, for each pixel, coordinates of the pixel in the first image and absorptiometry values designed to calculate the bone mineral density of the osseous body, referred to a surface area unit.

This type of method is known, in particular from the document U.S. Pat. No. 5,778,045. It is used in particular for examining osseous bodies of patients with the aim of providing a practitioner with information which is likely to aid practitioners in diagnosing osteoporosis.

With this type of method of the prior art, the mineral density calculated from the radiological data corresponds to a projection of the bone mineral density of the examined osseous body, in a plane perpendicular to the direction of incidence. The bone mineral density values thus calculated do not therefore provide any information on how this bone mineral density is distributed in this direction of incidence. In addition, the methods of the prior art do not take into account the individual morphological characteristics of the patients, and this can lead to errors in diagnosis. This limits the subsequent possibilities for the interpretation, by the practitioner, of the images thus obtained with a view to evaluating fracture risks and prescribing treatments. To overcome this disadvantage, and to obtain a three-dimensional representation of the bone mineral density, it is necessary to adopt another approach, namely tomodensitometry, for which it is necessary to perform a large number of tomodensitometry projections, which fact increases considerably the level of radiation exposure, to X-rays, of the body of the patient undergoing this examination.

BRIEF SUMMARY OF THE INVENTION

An object of the present invention is to overcome at least some of the disadvantages of the methods of the prior art.

According to an embodiment of the invention is a method as mentioned hereinabove which, in addition to the characteristics already mentioned, comprises a step (e) which consists in determining the value of a composite index using, on the one hand, first digitized radiological data, and, on the other hand, a three-dimensional generic model of said osseous body.

By virtue of these provisions, it is possible to obtain, with a very limited number of images, that is to say with a relatively low level of irradiation, an index which takes account of the three-dimensional shape of the osseous body examined. It is thus possible to ascertain the distribution in volume of this index, which can be especially representative of the bone mineral density. The method according to an embodiment of the invention thus provides, with a relatively low level of irradiation, a useful clinical index for evaluating the fracture risks and/or bone diseases and/or their treatment. The method according to an embodiment of the invention makes it possible not only to increase the precision of the measurements of the bone mineral density, but also to establish the macro-architecture of the osseous body analyzed. With a knowledge of the macro-architecture, it is possible, by taking into consideration various parameters of the bone mineral density alone, to refine the diagnosis of certain pathologies and of osteoporosis in particular.

It should be noted that the data deriving from the method according to the invention can be obtained by a technician who has been trained in how to carry out the method according to the invention, but that establishing a diagnosis from these data can be done only by a medically qualified practitioner.

In exemplary embodiments of the invention, one and/or more of the following provisions may also be implemented if appropriate:

prior to step (d) which consists in introducing the first radiological data into the calculation means, it comprises at least one of the following steps which consist in
  (a) scanning at least one anatomical part comprising said osseous body, by irradiating it in at least the first incidence with at least one beam of X-rays generated by at least one X-ray source and having an energy spectrum distributed about at least two energies,
  (b) detecting, by virtue of detection means, the energy of the radiation corresponding to the X-rays scanning, in the first incidence, each anatomical part comprising said osseous body and transmitted by each of the scanned parts, and delivering, from the detection means, signals corresponding to the radiation transmitted, and
  (c) digitizing and recording these signals delivered by the detection means and corresponding at least to the first incidence, in order to constitute the first radiological data;

the step (d) comprises the operation which consists in reconstructing at least a first two-dimensional image of the bone mineral density of each scanned part of said osseous body, using the first radiological data;

it also comprises a step (d') which consists in introducing, into the calculation means, second digitized radiological data from signals delivered by means of detection of X-rays and corresponding to pixels of a second image of the anatomical part comprising said osseous body and scanned with a beam of X-rays in a second incidence not parallel to the first incidence, and in which the second radiological data are introduced in step (e), for determining the value of the composite index;

prior to step (d') which consists in introducing the second radiological data into the calculation means, it comprises the following steps which consist in:
  (a') scanning at least one anatomical part comprising said osseous body, by irradiating it in the second incidence with a beam of X-rays having an energy spectrum distributed about at least one energy;
  (b') detecting, by virtue of the detection means, the energy of the radiation corresponding to the X-rays scanning, in the second incidence, each anatomical part comprising said osseous body and transmitted by each of the scanned parts, and delivering, from the detection means, signals corresponding to the radiation transmitted, and
  (c') digitizing and recording the signals delivered by the detection means and corresponding to the second incidence, in order to constitute the second radiological data;

the first and second radiological data are obtained respectively in the first incidence and second incidence, by two consecutive scans of said anatomical part, or by one simultaneous scan in the first incidence and second incidence, of said anatomical part;

the step (d) also comprises the operation which consists in reconstructing a second two-dimensional image, chosen from between a standard radiographic image and an image of the bone mineral density, of each scanned part of the body containing said osseous body, using the second radiological data;

the step (e) comprises at least one of the following subsidiary steps consisting in:
  ($e_1$) identifying, on at least the first image, predetermined markers corresponding to said osseous body,
  ($e_2$) determining in the three-dimension reference system, and by virtue of first means of reconstruction, the geometric position of each marker identified in step ($e_1$), and
  ($e_3$) determining, by virtue of second means of reconstruction, the three-dimensional shape of an actual model representing said osseous body, by deformation of a predetermined generic model, while at the same time keeping markers of this generic model in coincidence, during deformation, with the markers reconstructed by the first means of reconstruction;

the generic model is deformed in such a way that the actual model follows a shape which is as close as possible to an isometry of the generic model;

it comprises a step (g) which consists in determining, in a three-dimension reference system, and by virtue of third means of reconstruction, the geometric position of three-dimensional contours belonging to said osseous body, by bringing markers identified in step ($e_1$) into line with three-dimensional contours of the generic model which are projected onto at least the first image, and by performing a non-homogeneous geometric deformation of the generic model in order to improve the match between information originating from at least the first image and information representative of the actual model;

during step ($e_1$), some of the identified markers, called "non-stereo-corresponding control markers", are visible and identified only on a single image, and, during step ($e_2$), the geometric position of each non-stereo-corresponding control marker in the three-dimension reference system is estimated from the generic model, by displacing the non-stereo-corresponding control markers of the generic model, each on a straight line joining:
  on the one hand, the X-ray source to the origin of the image in which a projection of this non-stereo-corresponding control marker is visible and identifiable,
  and, on the other hand, the projection of this marker onto this image, the non-stereo-corresponding control markers thus being displaced to respective positions which minimize the global deformation of the generic model of the object to be observed;

during the operation ($e_3$), the value of the quadratic sum is minimized:

$$S = \lambda \cdot \sum_{i=1}^{m} k_i \cdot (x_i - x_{i0})^2,$$

where $\lambda$ is a constant coefficient, m is a whole number of imaginary springs joining each marker of the generic model to other markers of this model, $k_i$ is a predetermined value of stiffness of the imaginary spring of index i, $x_{i0}$ is the length of the imaginary spring of index i in the initial generic model, and $x_i$ is the length of imaginary spring of index i in the generic model during deformation;

during the step ($e_1$), at least some of the markers are stereo-corresponding control markers visible and identified on the first image and another image;

during the step ($e_3$), the geometric position of the stereo-corresponding control markers is directly calculated from measurements of position of the projections of these markers onto the first image and the other image;

it comprises a step (h) which consists in performing a radiographic calibration of the three-dimensional environment of said osseous body by defining the three-dimensional reference system in which are expressed the coordinates of each X-ray source and the detection means for each incidence;

during the operation (e), contour lines corresponding to limits of said osseous body and/or to lines of greater grey level density inside these limits are plotted on each image; and the composite index is a parameter chosen from among
  a specific parameter of the bone geometry, chosen from among the angle, length, surface and volume of an osseous part,
  a physical parameter chosen from the density and the mass of the osseous part,
  a mechanical parameter chosen from the section modulus (measurement of relative strength taking account of the three dimensions: depth, width, length) and the moments of inertia of an osseous part, and
  a chemical parameter chosen from the water composition, fat composition and bone composition of an anatomical part comprising said osseous body, or any combination of at least two of the preceding parameters; and the composite index is a combination of at least two parameters, of which
  one is chosen from among the specific parameters of the bone geometry and the physical parameters: the angle, length, surface, volume, bone mineral density and mass of an osseous part, and
  the other is chosen from among the chemical and physical parameters: the water composition, fat composition, bone composition of an anatomical part comprising the osseous body, and the section modulus and moments of inertia of an osseous part. It will be noted that, with the methods of the prior art, calculation of such an index was not possible.

According to another aspect, an embodiment of the invention concerns a device for radiographic imaging in three dimensions for implementing the method described above. This device comprises:
  calculation means designed to calculate first digitized radiological data from signals delivered by means of detection of X-rays and corresponding to pixels of a first image of an anatomical part comprising an osseous body and scanned, in a first incidence, with an X-ray beam having an energy spectrum distributed about at least two energies, these first data comprising, for each pixel, coordinates of the pixel in the first image and absorptiometry values designed to calculate the bone mineral density of the osseous body, referred to a surface area unit, and
  storage means for storing at least one three-dimensional generic model of said osseous body, characterized in that the calculation means are also designed to determine the value of a composite index using, on the one hand, first digitized radiological data, and, on the other hand, at least one three-dimensional generic model of said osseous body, stored in the storage means.

This exemplary device embodiment comprises, if appropriate, one and/or more of the following provisions:

it comprises radiation-generating means designed to generate, in at least a first incidence, at least one beam of X-rays having an energy spectrum distributed about at least two energies and to scan at least one anatomical part comprising said osseous body;

it comprises means of detection designed to detect the energy of the radiation corresponding to the X-rays scanning, in the first incidence, each anatomical part comprising said osseous body and transmitted by each of the scanned parts, and to deliver, from the detection means, signals corresponding to the radiation transmitted;

it comprises means for digitizing and recording the signals delivered by the detection means and corresponding at least to the first incidence, in order to constitute the first radiological data;

the radiation-generating means are also designed to generate, in a second incidence not parallel to the first incidence, a beam of X-rays having an energy spectrum distributed about at least one energy, and to scan at least one anatomical part comprising said osseous body;

the means of detection are also designed to detect the energy of the radiation corresponding to the X-rays scanning, in the second incidence, each anatomical part comprising said osseous body and transmitted by each of the scanned parts, and to deliver signals corresponding to the radiation transmitted;

the means of digitization and recording are also designed to digitize and record the signals delivered by the detection means and corresponding to the second incidence, in order to constitute second radiological data;

the radiation-generating means consist of a single X-ray radiation source generating alternately two X-ray beams, each corresponding to a different energy spectrum, this radiation source being movable, relative to said osseous body, in a plane comprising the first incidence and second incidence and also along an axis of translation perpendicular to this plane;

the detection means consist of a detector comprising a line of detection cells perpendicular to the axis of translation, the radiation source and the detector being aligned on a source-detector axis parallel to the plane comprising the first incidence and second incidence; and the means of reconstruction are designed to plot contours or points of the surface of said osseous body on an image of form:

$$Im(x, y) = \sum_{i \geq 1} a_i \cdot f_i \cdot (S_i(x, y)).$$

where
the $a_i$ are real coefficients,
the $f_i$ are functions of $\mathfrak{R}$ in $\mathfrak{R}$,
the $S_i(x,y)$ are the absorptiometry values for each pixel (x,y) of said image obtained with a radiation whose energy distribution corresponds to a spectrum i.

According to another aspect, an exemplary embodiment of the invention is a computer program for digital processing of radiographic images, this program executing an operation which consists in calculating first radiological data, from signals delivered by X-ray detection means and corresponding to pixels of a first image of an anatomical part comprising an osseous body and scanned, in a first incidence, with a beam of X-rays having an energy spectrum distributed about at least two energies, these first data comprising, for each pixel, coordinates of the pixel in the first image and absorptiometry values designed to calculate the bone mineral density of the osseous body, referred to a surface area unit. This program is characterized in that it executes an operation which consists in determining the value of a composite index using, on the one hand, first digitized radiological data and, on the other hand, a three-dimensional generic model of said osseous body stored in the storage means of a computer.

According to another aspect, an exemplary embodiment of the invention is a computer program product comprising program code means stored on a support readable by a computer, in order to execute the method according to the invention, when said program product is operating on a computer. This computer program product can comprise, for example, a CD-ROM, diskette, etc.

Other features, aims and advantages of the invention will become clear on reading the following description of a number of embodiments thereof.

BRIEF DESCRIPTION OF SEVERAL VIEWS OF THE DRAWINGS

The invention will also be better understood with the help of the drawings in which.

DETAILED DESCRIPTION OF THE INVENTION

In the various figures, the same reference labels designate identical or similar elements.

Figure 1:
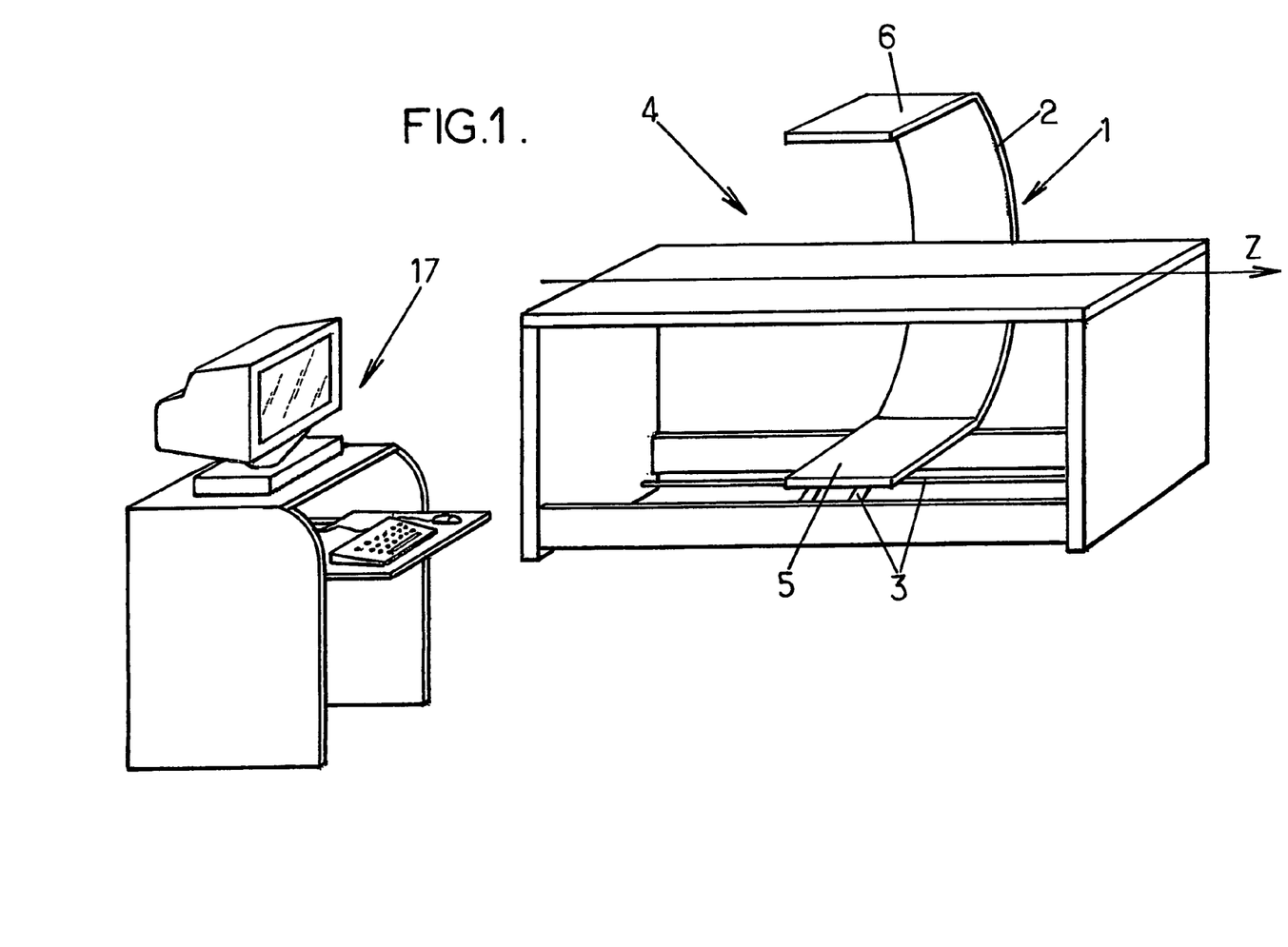
FIG. 1 is a diagrammatic representation, in perspective, of a radiographic imaging device according to one embodiment of the invention.

FIG. 1 shows an imaging device 1 for three-dimensional reconstruction of a composite index, such as the bone mineral density referred to a volume. This device comprises a mobile frame 2 which can be displaced by a motor on guides 3, in translation on a horizontal longitudinal axis Z and in rotation about this same horizontal axis Z.

This frame 2 encloses an observation field 4 in which a patient can be placed.

The mobile frame 2 comprises radiation-generating means and detection means.

These radiation-generating means and these detection means are of a type known to the skilled person (see, for example, document U.S. Pat. No. 5,778,045).

The radiation-generating means are formed by an X-ray source 5. They are designed to generate alternately an impulse corresponding to a high-energy spectrum and an impulse corresponding to a low-energy spectrum.

The detection means are formed by one or more detectors 6 which are arranged on a source-detector axis opposite the source 5 on the other side of the field 4. Of course, other types and other configurations of detectors could, if appropriate, be used in the context of the present invention. In particular, the respective locations of the generating means 5 and detection means 6 can be reversed if appropriate.

The frame 2 and the observation field 4 being movable in rotation with respect to one another about the horizontal axis Z, the relative position of the source-detector axis and of the field 4 can be modified by an angle of between 0 and 90 degrees, perpendicular to the horizontal axis Z. Thus, the radiation-generating means can emit the two beams, i.e. of high energy and low energy respectively, in several incidences, and in particular in two quasi-orthogonal incidences.

The detector 6 is designed to detect the energy of the X-rays arriving at and passing through an anatomical part of the patient being analyzed, this anatomical part comprising the osseous body of which a three-dimensional representation is sought and being scanned by the X-ray beams. This detector delivers signals corresponding to the radiation transmitted.

The frame 2 is controlled by a microcomputer 17 or other electronic control system.

The microcomputer 17 is equipped in particular with:
  recording means (the memory or memories of the microcomputer 17) for recording the signals delivered by the detector for each energy and for each incidence, and
  calculation means for reading these signals and reconstructing, for each incidence in which two energy spectrums are emitted and detected, first and second two-dimensional radiographic images of the anatomical part comprising the osseous body.

The device which has just been described functions as follows.

Figure 2:
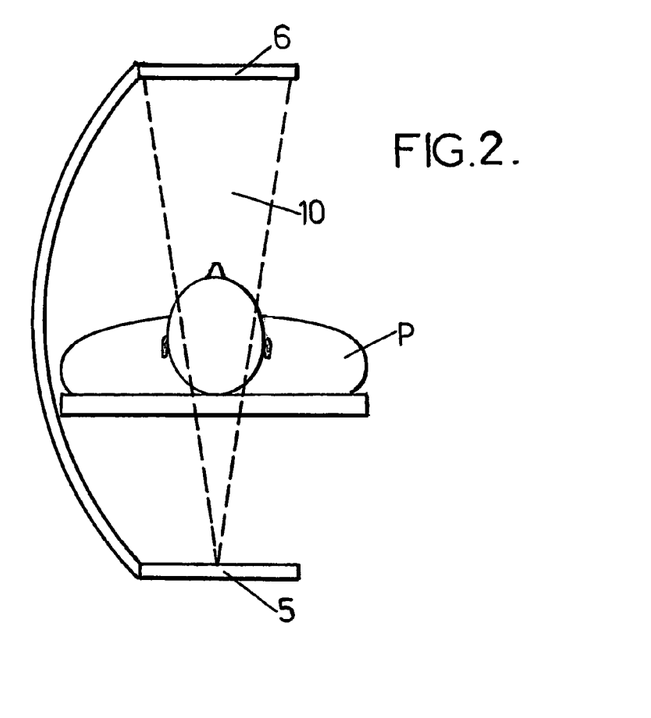
FIG. 2 is a diagrammatic end view of the radiation-generating means of the imaging device shown in FIG. 1.
Figure 3:
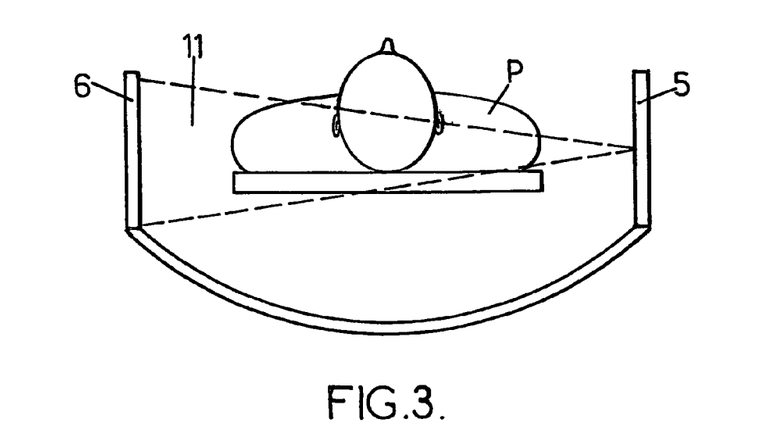
FIG. 3 is a diagrammatic end view analogous to that of FIG. 2, the respective position of the patient and of the radiation-generating means of the imaging device according to the invention having been turned approximately 90° in relation to their respective position in FIG. 2.

By means of the microcomputer 17, a first image of the bone mineral density and a second image of an anatomical part of a patient P are taken. As is shown in FIGS. 2 and 3, to do this the observation field 4 is scanned successively in one incidence, for example vertically, by beams 10 of high and low energy, then in another incidence, for example horizontally, also by at least one beam 11 of high and/or low energy.

During this movement, two digital images, for example an antero-posterior image and a lateral image respectively, of the examined part of the patient P are recorded in the memory of the microcomputer 17, and these images can be viewed on the screen of the microcomputer 17.

These two images correspond respectively to first and second radiological data which can be processed immediately or stored for later processing.

Figure 4:
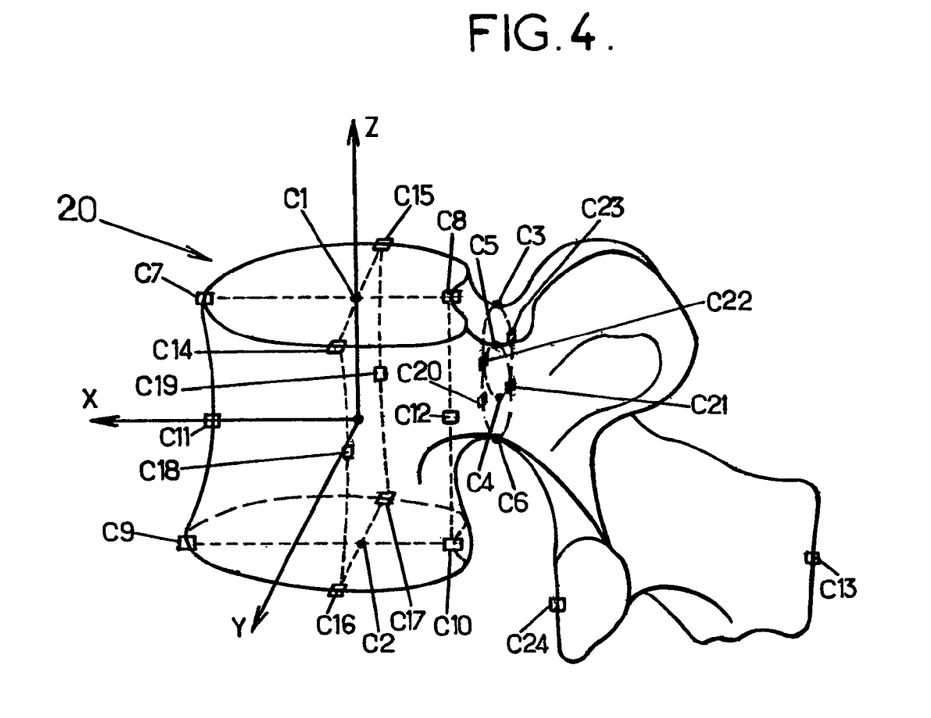
FIG. 4 is a diagrammatic perspective view of a vertebra of a patient examined by means of the device in FIG. 1.

Each of these images generally comprises several predetermined objects to be examined, for example vertebrae 20 such as the one shown diagrammatically in FIG. 4.

For each of these objects to be examined, the microcomputer 17 has, in its memory, a three-dimensional generic model. This generic model corresponds, for example, to a specific specimen or to an average form of the object in question, which generic model, in the latter case, is produced in advance by statistical methods and by analyzing a large number of similar objects.

When the radiographic images are displayed on the screen of the microcomputer 17, a technician can for example inform the microcomputer, in particular via a keyboard or mouse, of the nature of each object to be examined which is visible on the images, so that the microcomputer 17 determines the generic model corresponding to this object. This step can, if appropriate, be carried out before the examination in order in particular to help the user carry out the adjustments prior to acquisition of the images.

Moreover, the generic models used could also be models produced beforehand by medical imaging on the patient P. In this case, it may be possible for example, with the method according to the invention, to monitor the subsequent development of the patient P by means which are simpler, less costly and emit less radiation than conventional imaging by tomography.

The generic model of each object, for example of each vertebra 20 of a human skeleton, comprises:
  the coordinates of a plurality of control markers, in particular of the points corresponding to individual markers of this vertebra,
  and the coordinates of a large number of other markers of the object in question, for example numbering about 200 or more.

These coordinates can be expressed for example in a local reference system X, Y, Z. In the example in question, the axis Z corresponds to the "axial" direction of the vertebral column, the axis X is determined in such a way as to define with the axis Z the antero-posterior plane of the vertebra 20, the axis Y being perpendicular to the axes X, Z. Moreover, the origin O of the reference system X, Y, Z is placed at the centre of the two axial end faces of the body of the vertebra, the origin O moreover being positioned so that the axis Z passes through the upper axial face of the main part of the vertebra at a marker C1 such that the distance from this marker C1 to the front end C7 of the axial face is equal to about ⅔ of the total distance between the front end C7 and rear end C8 of the antero-posterior section of the upper axial face.

Figure 5:
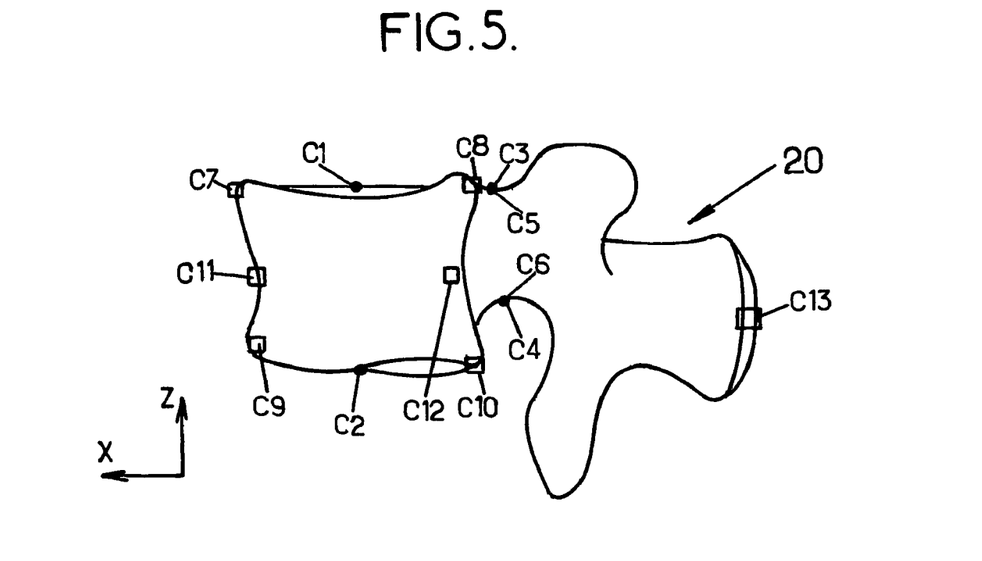
FIGS. 5 and 6 are a side view and front view, respectively, of the vertebra in FIG. 4, outlining part of the side and front views obtained by means of the device in FIG. 1.
Figure 6:
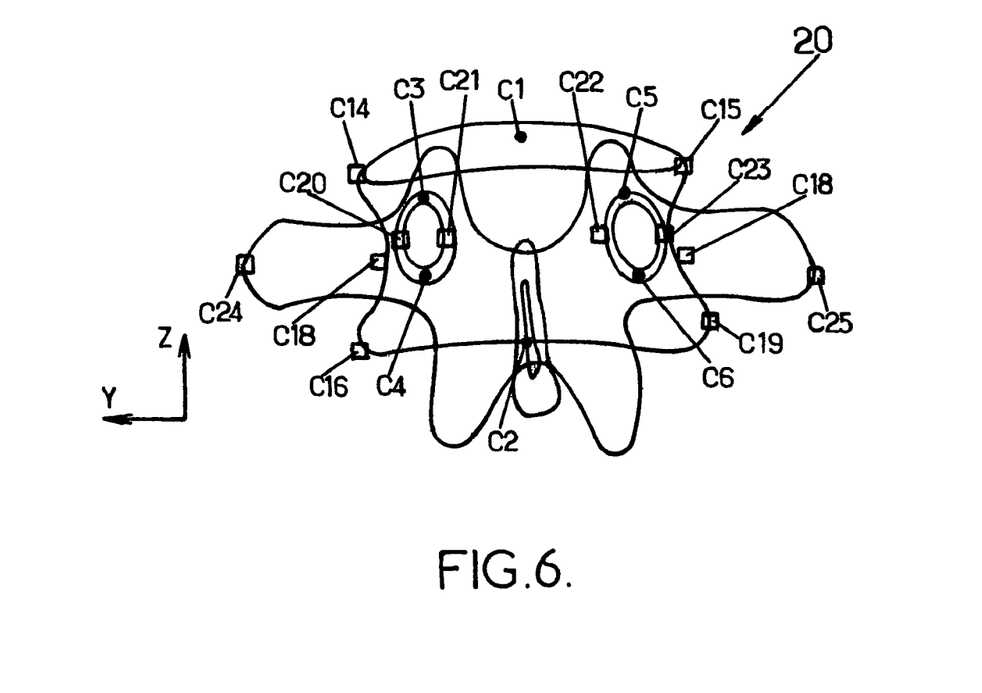

The various control markers C1-C25 are organized in two categories:
  "stereo-corresponding" control markers C1-C6 which are visible and identifiable both on the lateral image and on the antero-posterior image, these markers being 6 in number in the example in question (see FIGS. 4, 5 and 6),
  and "non-stereo-corresponding" control markers C7-C25 which are visible and identifiable on a single image, these markers being 19 in number in the example in question.

The technician identifies these different control markers for each object to be examined (for example the vertebrae) on each radiographic image, for example by "plotting" these markers on the screen of the micro-computer 17 by selecting them using the mouse and/or keyboard. The two images are also calibrated so as to be able to precisely measure the position of each marker of these images in a common reference system.

A geometric position of each control marker of each object is then determined in a three-dimension reference system, for example the X, Y, Z reference system or a reference system common to all the objects to be examined.

The position of the stereo-corresponding control markers C1-C6 is calculated directly from the measurement of the position of these points on the two images.

Moreover, the geometric position of each non-stereo-corresponding control marker C7-C25 in the three-dimension reference system is estimated from the generic model by moving each stereo-corresponding control marker C1-C6 of the generic model to its measured position, and by moving the non-stereo-corresponding control markers C7-C25 of the generic model, each on a straight line joining:

on the one hand, the source 5 to the origin of the radiographic image in which a projection of this non-stereo-corresponding control marker is visible and identifiable, and, on the other hand, the projection of this marker onto the radiographic image, the non-stereo-corresponding control markers thus being moved to respective positions which minimize the global deformation of the generic model of the object to be observed.

In particular, said deformation can be minimized by minimizing (for example by means of a gradient method) the value of the quadratic sum:

$$S = \frac{1}{2} \cdot \sum_{i=1}^{m} k_i \cdot (x_i - x_{i0})^2,$$

or more generally $$S = \lambda \cdot \sum_{i=1}^{m} k_i \cdot (x_i - x_{i0})^2,$$

where $\lambda$ is a predetermined constant coefficient, m is a whole number, not zero, representing a number of imaginary springs joining each control marker of the generic model to other control markers, $k_i$ is a predetermined coefficient of stiffness of the imaginary spring of index i, $x_{i0}$ is the length of the imaginary spring of index i in the non-deformed generic model, and $x_i$ is the length of imaginary spring of index i in the generic model during deformation.

Finally, the three-dimensional shape of an actual model representing the vertebra 20 of the patient P is calculated, the actual model being obtained by deformation of the generic model so as to maintain the coincidence of the control points of the generic model during deformation with the previously determined spatial position of the control points and so that this actual model follows a shape which is as close as possible to an isometry of the generic model, this time working on all of the points of the generic model.

The three-dimensional model of each object to be examined can be obtained in particular by the procedure known as kriging.

After the calculation of the three-dimensional model of the different objects to be examined, the micro-computer 17 can assemble all of the three-dimensional models of the different objects to be examined, as a function of the position of these different models in an absolute reference system common to all these objects, so as to obtain a three-diemensional model comprising, for example, the whole of the patient's spine.

Once set up, this three-dimensional model can be displayed on the screen of the micro-computer 17, or printed out, at the desired angle of vision. This overall model can also be moved on screen in accordance with the technician's commands.

By virtue of the exemplary embodiment of the method as described above, a three dimensional representation of a composite index is obtained. The first image being a projection in a plane of the bone mineral density and the second image being a conventional radiography, it is possible to obtain on one hand a tridimensional geometrical reconstruction of each vertebrae, and even of the rachis, and on the other hand, values of the projected bone mineral density for each one of these vertebrae. In this case, the composite index is a combination of physical parameters.

Knowing geometrical parameters determined from the tridimensional reconstruction and the bone mineral density data allows, for instance, to estimate fracture risks.

The exemplary embodiment of the method here described can be, of course, used for studying other bone structures than vertebrae.

For instance, are presented below results obtained from an exemplary embodiment of the method of the invention applied to femur studies.

According to this exemplary embodiment, twelve human femurs have been studied, nine of them were femal femurs, three of them were male femurs, all the donors were from 65 to 95 years old.

For these twelve femurs, on one hand a tridimensional reconstruction has been made from two perpendicular Dual energy X-ray Absorptiometry (DXA) images, and on the other hand projected bone mineral density measurements were performed from at least one of these DXA images.

From the tridimensional reconstruction of each femur has been calculated geometrical parameters such as the Femoral Head Diameter, the Neck-Shaft Angle, the Femoral Nech Axis Length and the Midneck Cross Section Area.

These parameters are particularly important for the prediction of the fracture risks as shown by A. Le Bras, S. Kolta, C. Roux, J. Fechtenbaum, W. Skalli, D. Mitton (2003): "The effect of 3-dimensional X-ray absorptiometry derived geometric parameters on proximal femur failure load prediction", ASBMR Congress 2003, Mineapolis, USA.

Indeed, these authors have used a statistical step-by-step method well known from skilled persons to perform a multiple linear regression. This method allowed to select, in a set of parameters, the parameters which were the most correlated to the failure risk. Indeed, the bone mineral density BMD, the Femoral Head Diameter D, the Midneck Cross Section Area S and the Neck-Shaft angle X, have been selected in a set of parameters further comprising the Femoral Neck Axis Length. A composite index constituted of a linear combination of these parameters is determined in this way.

For instance, for a particular set of experimental values, a composite index $\gamma$ is given by the relation:

$$\gamma = -1.302 \times 10^5 + 0.899 \times BMD - 0.382 \times D + 0.521 \times S + 0.258 \times X.$$

Figure 7:
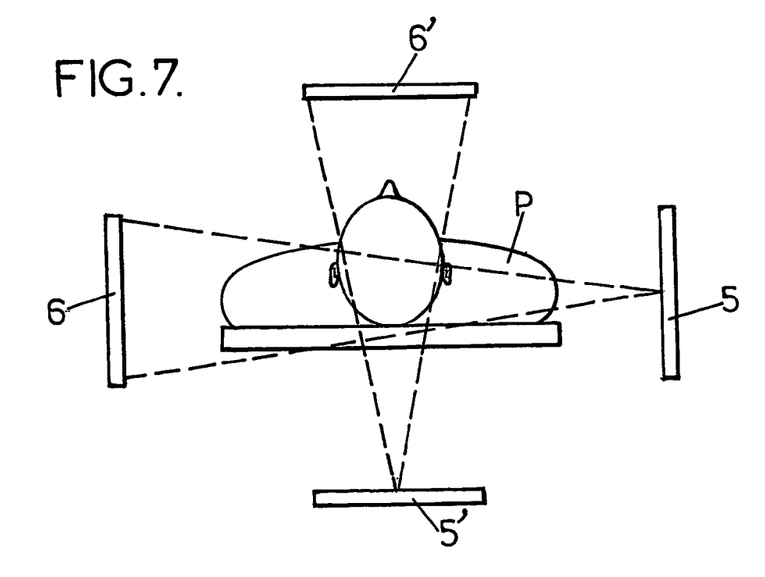
FIGS. 7 and 8 show respectively the fracture load measured on several femurs as a function on one hand of the bone mineral density (FIG. 7) measured on these femurs and on the other hand of a composite index (FIG. 8) corresponding to these femurs.
Figure 8:
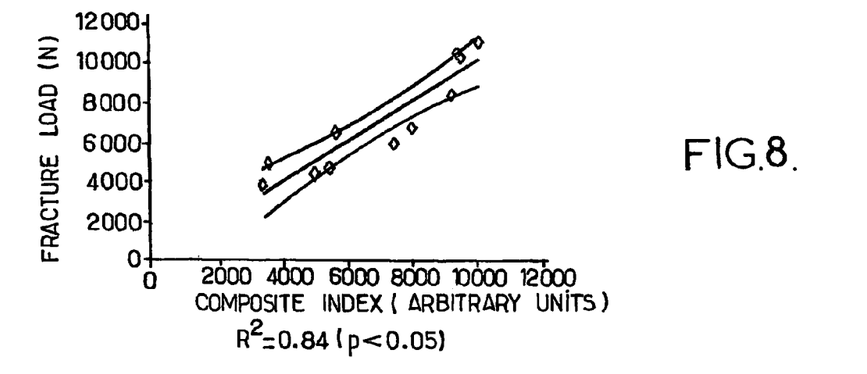

A. Le Bras et al. have then determined a linear regression coefficient between the composite index and the fracture load experimentally measured with mechanical tests, comprised between 0.70 and 0.85. In the above-mentioned publication, this value is 0.73 and for the results corresponding to FIG. 8, this value is 0.84, when the linear regression coefficient between the projected bone mineral density for a determined femoral neck area and the fracture load is only 0.62 and 0.68 respectively for the above-mentioned publication and FIG. 7.

Then, it is possible to deduce from the composite index determined in this way a predicted value for the fracture load.

A practitioner is thus provided with an effective examining tool which can be used for imaging any part, especially an osseous part, of the human or animal body and which is useful in particular for diagnosing osteoporosis or for monitoring certain diseases, also in the periods before and after surgical intervention.

Of course, it is also possible to calculate certain predetermined clinical indices which are associated with the geometry of the object examined and are estimated from the radiographic images (the case of osteoporosis for example).

Figure 9:
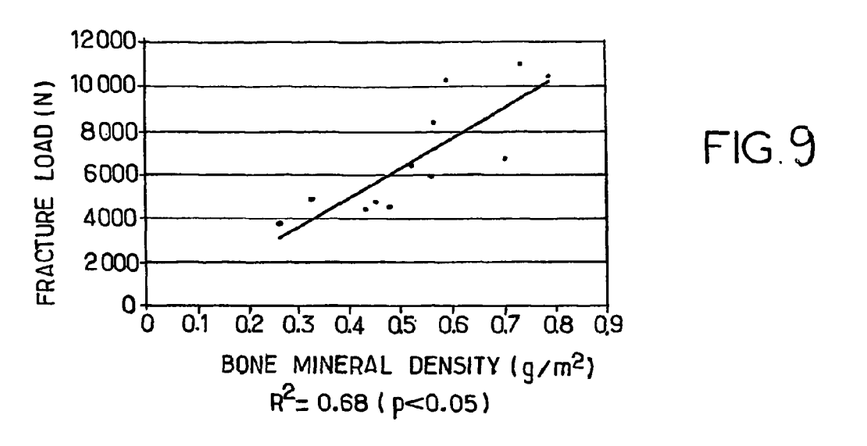
FIG. 9 is a diagrammatic end view, analogous to that in FIGS. 2 and 3, of a variant of the radiation-generating means of the imaging device according to the invention shown in FIG. 1.

As is shown in FIG. 9, it is possible to achieve simultaneous acquisition of the two radiographic images. To do so, it suffices to have two sources 5, 5' and two detectors 6, 6' arranged with their respective source-detector axes corresponding to two beams 10, 11 at incidences forming an angle of almost 90°.

It will be noted that the device according to the invention can comprise more than two sources 5, 5' and more than two detectors 6, 6', and it would be possible, if appropriate, for the incidences of these different sources of radiation not to be perpendicular with respect to one another.

It will also be noted that the method according to the invention can involve acquisition of more than two images, for example in more than two incidences respectively. If such is the case, it is then possible to perform plotting and reconstruction using the information corresponding to the different images obtained, in a manner analogous to what has been described above.

It will also be noted that the device according to the invention can comprise a single source 5 and one or more detectors 6, the source 5 being able to adopt at least two different relative positions with respect to the patient P, opposite the detector or detectors 6.

It will also be noted that the device according to the invention could if appropriate be used in non-medical radiology applications.

It goes without saying that in all cases the radiographic device 1 can also be used in two-dimensional radiography, over and above its use in three-dimensional imaging.

The device and the method according to the invention can be used to perform three-dimensional imaging starting from classical radiology images.

In this context, it will be noted that an image can be represented by $$\text{Im}(x, y) = \sum_{i \geq 1} a_i \cdot f_i \cdot (S_i(x, y)).$$

where
the $a_i$ are real coefficients,
the $f_i$ are functions of $\Re$ in $\Re$,
the $S_i(x,y)$ are the absorptiometry values for each pixel $(x,y)$ of said image obtained with a radiation whose energy distribution corresponds to a spectrum i.

In general, the functions $f_i$ are logarithmic functions.

The coefficients $a_i$ are determined by standardization and by study of the environment of the soft tissues surrounding the bone tissues.

If $a_1=1$, $a_2=0$, $f_1$ the function identity and $f_2$ whatever, Im corresponds to $S_1$ (single-energy case).

If $a_1$ and $a_2$ (with i=2) are determined by standardization and if the functions $f_1$ and $f_2$ are logarithmic functions, Im corresponds to the dual-energy case, such as, for example, in the DXA technique (Dual-energy X-ray Absorptiometry).

In the device according to the invention, the means of reconstruction can be designed to plot contours or points of the surface of said osseous body on an image such as defined above. In this case, the device according to the invention permits reconstruction of a three-dimensional actual model of an osseous body using one or more images obtained from two different energy spectra (i=2) or from a single-energy radiation (i=1). This actual model is moreover hot necessarily representative of the bone mineral density if it is reconstructed from classical radiographic images.

Therefore, the device according to the invention can include a specific mode for three-dimensional reconstruction of the bone mineral density, or of another composite index, and a mode for three-dimensional reconstruction from classical radiographic images.

Furthermore, instead of using control markers C1-C25 defined in advance on each generic model, it would be possible to determine and spatially position the control markers using contour lines of the object to be observed which are visible on one or other of the two radiographic images.

To this end, the following procedure in particular could be followed:
a) contour lines corresponding to limits of the object observed and/or to lines of greater grey level density inside these limits are plotted on each radiographic image,
b) a generic model is created which is readjusted by adapting the size of the generic model and the position of this generic model in the the X, Y, Z reference system, so that the respective projections of the generic model readjusted using the two incidences of the beams 10, 11 correspond substantially to the two radiographic images,
c) markers of the generic model are selected whose projections on at least one of the radiographic images from the source 5, and in the corresponding incidence, are closest to the contour lines plotted during step (b),
d) the three-dimensional contours defined by the tangency of the X-rays with the object to be observed are calculated, in the initial position,
e) the determination of the initial position of the generic model is refined by bringing markers identified in the two radiographic images into line with the three-dimensional contours projected in these two radiographic images,
f) a non-homogeneous geometric deformation (for example kriging) of the generic model is applied in order to improve the match between the information from the image and the model thus reconstructed.

It will also be noted that the method according to the invention can include a step (h) which consists in performing a radiographic calibration of the three-dimensional environment of said osseous body by defining the three-dimensional reference system in relation to the coordinates, expressed in this reference system, of each X-ray source and of the detection means for each incidence.

Figure 10:
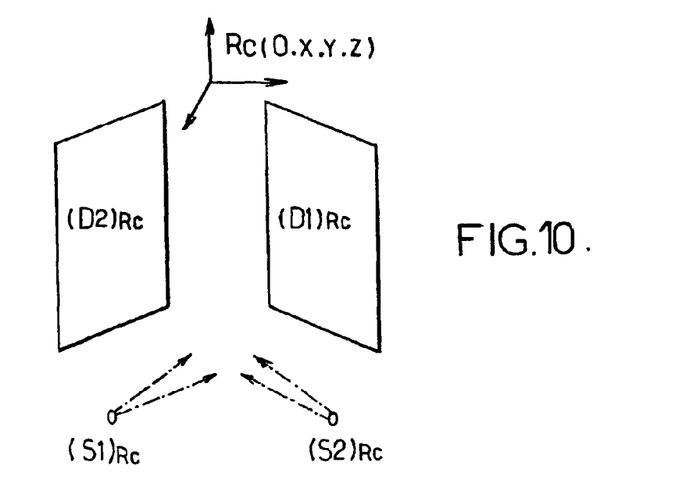
FIG. 10 is a diagrammatic representation of the device according to the invention located in a three-dimension reference system.

This operation is illustrated in FIG. 10.

In FIG. 10:
Rc (O, x, y, z) is the three-dimensional reference system with which it is possible to obtain the three-dimensional coordinates of the whole of the radiographic environment for each incidence, after calibration,
$(S1)_{Rc}$ represents the position of the X-ray source emitting with incidence 1, whose coordinates are expressed in the marker Rc following calibration, $(S2)_{Rc}$ represents the position of the X-ray source emitting with incidence 2, whose coordinates are expressed in the marker Rc following calibration, $(D1)_{Rc}$ represents the means of detection of X-rays originating with incidence 2, whose coordinates are expressed in the marker Rc, and $(D2)_{Rc}$ represents the means of detection of X-rays originating with incidence 1, whose coordinates are expressed in the marker Rc.

Once all these coordinates have been determined by a technique known to the person skilled in the art, the projections corresponding to the images of the osseous body to be analyzed can be very precisely positioned in this reference system, to permit plotting of the control markers in it.

It will be noted that it is possible to obtain beams having an energy spectrum distributed about several energies either with different energy impulses, as indicated above, or with filters, or any other method known to the skilled person.

Likewise, instead of obtaining radiographic images by scanning an anatomical part, it is possible to use a conical beam with a plane sensor.

The above U.S. patent and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. Method for radiographic imaging, comprising:
   (a) introducing, into calculation means, digitized radiological data from signals delivered by means of detection of X-rays and corresponding to pixels of an image of an anatomical part comprising an osseous body having a three-dimensional shape and scanned, in an incidence, with a beam of X-rays having an energy spectrum distributed about at least two energies, the digitized radiological data comprising, for each pixel, coordinates of the pixel in the image and absorptiometry values designed to calculate a bone mineral density of the osseous body, in units of a surface area; and
   (b) determining a value of a composite index using a processor of a radiographic image display device based on the digitized radiological data, and based on a three-dimensional generic model of said osseous body produced prior to generating the digitized radiological data from the scanned signals;
   wherein the composite index includes at least one of: an angle of bone geometry of an osseous part, a length of bone geometry of an osseous part, a surface of bone geometry of an osseous part, a volume of bone geometry of an osseous part, a bone mineral density of an osseous part, a mass of an osseous part, a water composition of an anatomical part comprising the osseous body, a fat composition of an anatomical part comprising the osseous body, a bone composition of an anatomical part comprising the osseous body, a section modulus of an osseous part, or moments of inertia of an osseous part.

2. Method according to claim 1, further comprising, prior to (a) introducing the radiological data into the calculation means:
   (c) scanning at least one anatomical part comprising said osseous body, by irradiating the osseous body in at least the incidence with at least one beam of X-rays having an energy spectrum distributed about at least two energies,
   (d) detecting, by virtue of detection means, the energy of the radiation corresponding to the X-rays scanning, in the incidence, each anatomical part comprising said osseous body and transmitted by each of the scanned parts, and delivering, from the detection means, signals corresponding to the radiation transmitted, and
   (e) digitizing and recording these signals delivered by the detection means and corresponding at least to the incidence, in order to constitute the radiological data.

3. Method according to claim 1, in which (a) introducing comprises reconstructing at least a two-dimensional image of the bone mineral density of each scanned part of said osseous body, using the radiological data.

4. Method according to claim 1, wherein said digitized radiological data are first digitized radiological data, wherein said incidence is a first incidence, the method also comprising (a') introducing, into the calculation means, second digitized radiological data from signals delivered by means of detection of X-rays and corresponding to pixels of a second image of the anatomical part comprising said osseous body and scanned with a beam of X-rays in a second incidence not parallel to the first incidence, and in which the second radiological data are introduced in (b), determining the value of the composite index.

5. Method according to claim 4, in which, prior to (a') introducing the second radiological data into the calculation means, further including:
   (c') scanning at least one anatomical part comprising said osseous body, by irradiating it in the second incidence with a beam of X-rays having an energy spectrum distributed about at least one energy;
   (d') detecting, by virtue of the detection means, the energy of the radiation corresponding to the X-rays scanning, in the second incidence, each anatomical part comprising said osseous body and transmitted by each of the scanned parts, and delivering, from the detection means, signals corresponding to the radiation transmitted, and
   (e') digitizing and recording the signals delivered by the detection means and corresponding to the second incidence, in order to constitute the second radiological data.

6. Method according to claim 5, in which the first and second radiological data are obtained respectively in the first incidence and second incidence, by two consecutive scans of said anatomical part.

7. Method according to claim 5, in which the first and second radiological data are obtained by simultaneous scanning, in the first incidence and the second incidence, of said anatomical part.

8. Method according to claim 4, in which (a) introducing comprises reconstructing a second two-dimensional image, chosen from between a standard radiographic image and an image of the bone mineral density, of each scanned part of the body containing said osseous body, using the second radiological data.

9. Method according to claim 1, in which (b) determining comprises:
   ($b_1$) identifying, on at least the image, predetermined markers corresponding to said osseous body,
   ($b_2$) determining in a three-dimension reference system, and by virtue of first means of reconstruction, a geometric position of each marker identified in ($b_1$) the identifying, and
   ($b_3$) determining, by virtue of second means of reconstruction, the three-dimensional shape of an actual model representing said osseous body, by deformation of a predetermined generic model while at the same time keeping markers of this generic model in coincidence, during deformation, with the markers reconstructed by the first means of reconstruction.

10. Method according to claim 9, in which the generic model is deformed in such a way that the actual model follows a shape which is as close as possible to an isometry of the generic model.

11. Method according to claim 9, comprising a (g) which consists in determining, in a three-dimension reference system, and by virtue of third means of reconstruction, the geometric position of three-dimensional contours belonging to said osseous body, by bringing markers identified in ($b_1$) into line with three-dimensional contours of the generic model which are projected onto at least the image, and by performing a non-geometric deformation of the generic model in order to improve a match between information originating from at least the first image and information representative of the actual model.

12. Method according to claim 9, in which:
during the ($b_1$) identifying, some of the identified markers, called non-stereo-corresponding control markers, are visible and identified only on a single image,
and, during the ($b_2$) determining, the geometric position of each non-stereo-corresponding control marker in the three-dimension reference system is estimated from the generic model, by displacing the non-stereo-corresponding control markers of the generic model, each on a straight line joining:
the X-ray source to the origin of the image in which a projection of this non-stereo-corresponding control marker is visible and identifiable,
and, the projection of this marker onto this image,
the non-stereo-corresponding control markers thus being displaced to respective positions which minimize the global deformation of the generic model of the object to be observed.

13. Method according to claim 12, in which, during the ($b_3$) determining, the value of the quadratic sum is minimized:

$$S = \lambda \cdot \sum_{i=1}^{m} k_i \cdot (x_i - x_{i0})^2,$$

where $\lambda$ is a constant coefficient, m is a whole number of imaginary springs joining each marker of the generic model to other markers of this model, $k_i$ is a predetermined value of stiffness of the imaginary spring of index i, $x_{i0}$ is the length of the imaginary spring of index i in the initial generic model, and $x_i$ is the length of imaginary spring of index i in the generic model during deformation.

14. Method according to claim 9, in which:
during the ($b_1$) identifying, at least some of the markers are stereo-corresponding control markers visible and identified on the first image and another image,
and, during the ($b_3$) determining, the geometric position of the stereo-corresponding control markers is directly calculated from measurements of position of the projections of these markers onto the first image and the other image.

15. Method according to claim 1, comprising (h) performing a radiographic calibration of the three-dimensional environment of said osseous body by defining a three-dimensional reference system in which are expressed the coordinates of each X-ray source and of the detection means for each incidence.

16. Method according to claim 1, in which, during the (b) determining, contour lines corresponding to limits of said osseous body and/or to lines of greater grey level density inside these limits are plotted on each image.

17. Method according to claim 1, in which the composite index is a parameter chosen from among a combination of
a specific parameter of the bone geometry, chosen from among the angle, length, surface and volume of the osseous part,
with at least one of the following parameters:
a physical parameter chosen from the bone mineral density and mass of the osseous part,
a mechanical parameter chosen from the section modulus and moments of inertia of the osseous part, and
a chemical parameter chosen from the water composition, fat composition and bone composition of the anatomical part comprising said osseous body.

18. Method according to claim 1, in which the composite index is a combination of at least two parameters, of which at least one of
one is chosen from among specific parameters of the bone geometry and the physical parameters: the angle, length, surface, volume, bone mineral density and mass of the osseous part, and
the other is chosen from among the chemical and physical parameters: the water composition, fat composition, bone composition of the anatomical part comprising the osseous body, and the section modulus and moments of inertia of the osseous part.

19. Device for radiographic imaging, comprising:
a calculation means designed to calculate digitized radiological data from signals delivered by means of detection of X-rays and corresponding to pixels of an image of an anatomical part comprising an osseous body having a three-dimensional shape and scanned, in an incidence, with a beam of X-rays having an energy spectrum distributed about at least two energies, these comprising, for each pixel, coordinates of the pixel in the image and absorptiometry values designed to calculate a bone mineral density of the osseous body, in units of a surface area unit, and
a storage means for storing at least one three-dimensional generic model of said osseous body, the at least one three-dimensional generic model produced prior to generating the digitized radiological data from the scanned signals,
characterized in that the calculation means are also designed to determine a value of a composite index based on the digitized radiological data, and based on at least one three-dimensional generic model of said osseous body, stored in the storage means;
wherein the composite index includes at least one of: an angle of bone geometry of an osseous part, a length of bone geometry of an osseous part, a surface of bone geometry of an osseous part, a volume of bone geometry of an osseous part, a bone mineral density of an osseous part, a mass of an osseous part, a water composition of an anatomical part comprising the osseous body, a fat composition of an anatomical part comprising the osseous body, a bone composition of an anatomical part comprising the osseous body, a section modulus of an osseous part, or moments of inertia of an osseous part.

20. Device according to claim 19, comprising in addition:
radiation-generating means designed to generate, in at least the incidence, at least one beam of X-rays having an energy spectrum distributed about at least two energies and to scan at least one anatomical part comprising said osseous body,
means of detection designed to detect the energy of the radiation corresponding to the X-rays scanning, in the incidence, each anatomical part comprising said osseous body and transmitted by each of the scanned parts, and to deliver, from the detection means, signals corresponding to the radiation transmitted, means for digitizing and recording the signals delivered by the detection means and corresponding at least to the incidence, in order to constitute the radiological data.

21. Device according to claim 20, wherein said incidence is a first incidence, wherein:

the radiation-generating means are also designed to generate, in a second incidence not parallel to the first incidence, a beam of X-rays having an energy spectrum distributed about at least one energy, and to scan at least one anatomical part comprising said osseous body, the means of detection are also designed to detect the energy of the radiation corresponding to the X-rays scanning, in the second incidence, each anatomical part comprising said osseous body and transmitted by each of the scanned parts, and to deliver signals corresponding to the radiation transmitted, the means of digitization and recording are also designed to digitize and record the signals delivered by the detection means and corresponding to the second incidence, in order to constitute second radiological data.

22. Device according to claim 20, wherein said incidence is a first incidence, wherein:

the radiation-generating means consist of a single X-ray radiation source generating alternately two X-ray beams, each corresponding to a different energy spectrum, this radiation source being movable, relative to said osseous body, in a plane comprising the first incidence and also along an axis of translation perpendicular to this plane, and in which the detection means consist of a detector comprising a line of detection cells perpendicular to the axis of translation, the radiation source and the detector being aligned on a source-detector axis parallel to the plane comprising the first incidence.

23. Device according to claim 19, in which the calculation means are designed to plot contours or points of the surface of said osseous body on an image of form:

$$\mathrm{Im}(x, y) = \sum_{i \geq 1} ai \cdot fi \cdot (Si(x, y)).$$

where the $a_i$ are real coefficients,
the $f_i$ are functions from $\Re$ to $\Re$,
the $S_i(x,y)$ are the absorptiometry values for each pixel (x,y) of said image obtained with a radiation whose energy distribution corresponds to a spectrum i.

24. Computer program product of manufacture that includes a non-transitory computer readable medium storing a sequence of instructions which, when executed by a processor of a radiographic image display device, causes the processor of the radiopraphic image display device to execute a process for digital processing of radiographic images, the process comprising:

calculating radiological data, from signals delivered by an X-ray detection means and corresponding to pixels of an image of an anatomical part comprising an osseous body having a three-dimensional shape and scanned, in an incidence, with a beam of X-rays having an energy spectrum distributed about at least two energies, these data comprising, for each pixel, coordinates of the pixel in the image and absorptiometry values designed to calculate a bone mineral density of the osseous body, in units of a surface area unit; and determining a value of a composite index based on the digitized radiological data, and based on a three-dimensional generic model of said osseous body stored in a storage means, the three-dimensional generic model of said osseous body produced prior to generating the digitized radiological data from the scanned signals;

wherein the composite index includes at least one of: an angle of bone geometry of an osseous part, a length of bone geometry of an osseous part, a surface of bone geometry of an osseous part, a volume of bone geometry of an osseous part, a bone mineral density of an osseous part, a mass of an osseous part, a water composition of an anatomical part comprising the osseous body, a fat composition of an anatomical part comprising the osseous body, a bone composition of an anatomical part comprising the osseous body, a section modulus of an osseous part, or moments of inertia of an osseous part.

25. Computer program product of manufacture that includes a non-transitory computer readable medium storing a sequence of instructions which, when executed by a processor of a radiographic image display device, causes the processor of the radiographic image display device to execute the process of claim 1.

* * * * *